(12) United States Patent
Piron et al.

(10) Patent No.: US 10,207,024 B2
(45) Date of Patent: Feb. 19, 2019

(54) BIODEGRADABLE SINGLE-PHASE COHESIVE HYDROGELS

(71) Applicant: LABORATOIRES VIVACY, Archamps (FR)

(72) Inventors: Estelle Marie Piron, Saint Etienne de Cuine (FR); Guy Vitally, Le Bourget du Lac (FR)

(73) Assignee: LABORATOIRES VIVACY, Archamps (FR)

( * ) Notice: Subject to any disclaimer, the term of this patent is extended or adjusted under 35 U.S.C. 154(b) by 0 days.

(21) Appl. No.: 15/812,588

(22) Filed: Nov. 14, 2017

(65) Prior Publication Data

US 2018/0064846 A1 Mar. 8, 2018

Related U.S. Application Data

(60) Division of application No. 14/164,592, filed on Jan. 27, 2014, now Pat. No. 9,919,076, which is a continuation of application No. 12/746,639, filed as application No. PCT/EP2008/067029 on Dec. 8, 2007, now abandoned.

(30) Foreign Application Priority Data

Dec. 7, 2007 (FR) ..................... 07 59641

(51) Int. Cl.
| | |
|---|---|
| *A61K 8/73* | (2006.01) |
| *C08L 5/00* | (2006.01) |
| *A61K 31/738* | (2006.01) |
| *A61K 8/04* | (2006.01) |
| *A61L 27/26* | (2006.01) |
| *A61L 27/52* | (2006.01) |
| *A61L 27/58* | (2006.01) |
| *A61Q 19/08* | (2006.01) |

(52) U.S. Cl.
CPC .............. *A61L 27/26* (2013.01); *A61K 8/042* (2013.01); *A61K 8/731* (2013.01); *A61K 8/733* (2013.01); *A61K 8/735* (2013.01); *A61K 8/736* (2013.01); *A61K 31/738* (2013.01); *A61L 27/52* (2013.01); *A61L 27/58* (2013.01); *A61Q 19/08* (2013.01); *A61K 2800/594* (2013.01); *A61K 2800/91* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 4,582,865 A | 4/1986 | Balazs et al. | |
| 4,716,154 A | 12/1987 | Malson et al. | |
| 6,224,893 B1 | 5/2001 | Langer et al. | |
| 6,685,963 B1 | 2/2004 | Taupin et al. | |
| 6,921,819 B2 | 7/2005 | Piron et al. | |
| 8,052,990 B2 | 11/2011 | Hermitte et al. | |
| 2003/0148995 A1 | 8/2003 | Piron et al. | |
| 2005/0281880 A1 | 12/2005 | Wang | |
| 2006/0105022 A1 | 5/2006 | Yokokawa et al. | |
| 2006/0194758 A1 | 8/2006 | Lebreton | |
| 2007/0077292 A1 | 4/2007 | Pinsky | |
| 2007/0196426 A1 | 8/2007 | Hermitte et al. | |
| 2008/0119930 A1 | 5/2008 | Osada et al. | |

FOREIGN PATENT DOCUMENTS

| | | |
|---|---|---|
| AU | 5766796 A | 11/1996 |
| EP | 0 466 300 A2 | 1/1992 |
| EP | 1 505 093 A1 | 2/2005 |
| EP | 1 505 093 B1 | 9/2010 |
| FR | 2 733 427 A1 | 10/1996 |
| FR | 2 861 734 A1 | 5/2005 |
| FR | 2 865 737 A1 | 8/2005 |
| GB | 2 151 244 A | 7/1985 |
| JP | 8-504841 A | 5/1996 |
| JP | 8-319231 A | 12/1996 |
| JP | 4709956 B2 | 6/2011 |
| WO | 94/01468 A1 | 1/1994 |
| WO | 96/33751 A1 | 10/1996 |
| WO | 99/01143 A1 | 1/1999 |
| WO | 00/46253 A1 | 8/2000 |
| WO | 03/093327 A1 | 11/2003 |
| WO | 2004/092222 A2 | 10/2004 |
| WO | 2005/061611 A1 | 7/2005 |
| WO | 2005/085329 A1 | 9/2005 |
| WO | 2005/110505 A2 | 11/2005 |

(Continued)

OTHER PUBLICATIONS

Jun. 2, 2015 Notice of Reasons for Rejection issued in Japanese Application No. 2014-130602.
Definition of "Semi-Interpenetrating Polymer Network (SIPN)," IUPAC Compendium of Chemical Terminology, 2nd Edition, 1997.
Definition of "Interpenetrating Polymer Network (IPN)," IUPAC Compendium of Chemical Terminology, 2nd Edition, 1997.
"What is Hyaluronic Acid?", Vivacy Laboraties, pp. 1-4, http://www.vivacy.eu/technology.html, retrieved Jan. 21, 2015.
Rosiak et al, "Radiation Formation of Hydrogels for Biomedical Applications," Institute of Applied Radiation Chemistry, Technical University of Lodz Wroblewskiego 15, 93-590 Lodz, Poland, pp. 1-50, IAEA, Dec. 2002.

(Continued)

*Primary Examiner* — David J Blanchard
*Assistant Examiner* — Alissa Prosser
(74) *Attorney, Agent, or Firm* — Oliff PLC

(57) ABSTRACT

A process of preparing a biodegradable single-phase cohesive hydrogel composition includes preparing 2 to 5 hydrogels that are independently crosslinked so that each hydrogel has a degree of crosslinking in a range from 0.02 to 0.4, and mixing the 2 to 5 hydrogels to obtain a homogenous mixture of 2 to 5 intertwined hydrogels that interpenetrate each other to form a single phase without covalent bonding between the hydrogels, wherein each hydrogel is prepared by a process that comprises independently crosslinking a polymer and the total polymer concentration of the composition is in a range from 5 to 50 mg/g.

22 Claims, No Drawings

(56) References Cited

FOREIGN PATENT DOCUMENTS

| WO | 2006/013612 A1 | 2/2006 |
|---|---|---|
| WO | 2007/028258 A2 | 3/2007 |

OTHER PUBLICATIONS

Barbucci, Hydrogels Biological Properties and Applications, Samal et al., "Hybrid Hydrogels Based on Poly (vinylalcohol)-Chitosan Blends and Relevant CNT Composites," pp. 67-78, 2009.

"Hydrophophilic Polymers," Polymer Science—Sigma-Aldrich, http://www.sigmaaldrich.com/materials-science/material-science-products.html?TablePage=16372116, retrieved Mar. 16, 2012.

Matteini et al, "Structural Behavior of Highly Concentrated Hyaluronan," Biomacromolecules, vol. 10, pp. 1516-1522, 2009.

Selyanin et al., Hyaluronic Acid Preparation, Properties, Application in Biology and Medicine, Chapter 5, "Chemical Modifications, Solid Phase, Radio-Chemical and Enzymatic Transformation of Hyaluronic Acid," pp. 121-141, 2015.

Robeson, Polymer Blends A Comprehensive Review, excerpt of Chapter 2.1, "Thermodynamic relationships," 2007.

Elisseeff "Structure starts to gel," Nature Materials, vol. 7, pp. 271-273, Apr. 2008.

Chapter 4 of "Hyaluronic Acid: Preparation, Properties, Application in Biology and Medicine," First Edition, Mikhail A. Selyanin, Petr Ya. Boykov, and Vladimir N. Khabarov, published 2015 by John Wiley & Sons, Ltd.

Chapter 6 of "Hyaluronic Acid: Preparation, Properties, Application in Biology and Medicine," First Edition, Mikhail A. Selyanin, Petr Ya. Boykov, and Vladimir N. Khabarov, published 2015 by John Wiley & Sons, Ltd.

Podzimek et al., "Solution Properties of Hyaluronic Acid and Comparison of SEL-MALS-VIS Data with Off-Line Capillary Viscometry," Journal of Applied Polymer Science, vol. 116, 3013-3020 (2010).

Lapcik et al., "Flyaluronan: Preparation, Structure, Properties, and Applications," Chemical Reviews, vol. 98, No. 8, 2663-2684 (1998) ("Lapcik").

IUPAC Gold Book, "network" entry, <https://goldbook.iupac.org/html/N/N04112.html>, accessed May 15, 2017.

Wikipedia entry for "Phase" last updated Jul. 5, 2015; https://en.wikipedia.org/wiki/Phase_(matter).

American Academy of Orthopaedic Surgeons (AAOS), "Viscosupplementation Treatment for Arthritis", 2009, http://orthoinfo.aaos.org/topic.cfm?topic=a00217.

Interpenetrating polymer network, retrieved from http://en.wikipedia.org/w/index.php?title=Interpenetrating_polymer_network&oldid=442086665 (Jul. 29, 2011).

Esthelis—Detailed Scientific Information (date unknown but prior to Apr. 4, 2013).

BIODEGRADABLE SINGLE-PHASE COHESIVE HYDROGELS

This is a Division of application Ser. No. 14/164,592 filed Jan. 27, 2014, which is a Continuation of application Ser. No. 12/746,639 filed Aug. 19, 2010, which is a National Stage Entry of Application No. PCT/EP2008/067029 filed Dec. 8, 2008, which claims priority to FR 0759641 filed Dec. 7, 2007. The disclosures of the prior applications are hereby incorporated by reference herein in their entireties.

The invention relates to the field of crosslinked biodegradable hydrogels having esthetic applications, for example, or medicinal applications.

Mention will be made, among the esthetic applications, for example, of the filling in of fine lines, wrinkles and skin defects and the increase in the volumes.

Mention will be made, among the medical applications, for example, of periurethral injection for the treatment of urinary incontinence by sphincter insufficiency, postsurgical injection for preventing peritoneal adhesions in particular, injection for replacement of deficient biological fluids (in the joints in particular for replacing deficient synovial fluid) and injection subsequent to surgery for far-sightedness by scleral incisions with a laser.

In all these applications, the hydrogels used have to exhibit optimized properties in terms of persistence in vivo, of rheology and of viscosity in order to guarantee good "injectability", these hydrogels being applied by injection using needles of variable sizes depending on the applications but which have to remain as fine as possible in order to minimize postinjection reactions.

The optimization of these various properties results in compromises which are often not very satisfactory as they are sometimes incompatible. Specifically, in order to increase the persistence in vivo, it is advisable to increase the degree of crosslinking but, on increasing the degree of crosslinking, the "injectability" is necessarily reduced.

Numerous solutions have been proposed and mention will be made, among these, of compositions based on permanent or very slowly biodegradable particles dispersed in an injection vector, for example PMMA (polymethyl methacrylate) particles in a collagen gel (Artecoll), acrylic hydrogel particles in a crosslinked sodium hyaluronate gel (Dermalive, Dermadeep) or polylactic acid or polylactide (PLA) particles in an aqueous vector (New Fill, Sculptra, the PLA being resorbed in 1 to 4 years depending on the size of the particles).

These implants are subject to controversy as a result of the potential side effects due to the solid particles, in particular if they are not round and if they have a permanent nature. Mention may be made, among the complications listed, of inflammation, edema and granuloma.

Mention may also be made of biodegradable implants based on crosslinked or noncrosslinked polysaccharides essentially based on sodium hyaluronate.

To get round these disadvantages, in the majority of the documents of the prior art, for example in application FR 2 865 737, filed by Anteis S.A., or in FR 2 861 734, filed by Corneal Industrie S.A., the products described are obtained by a crosslinking carried out on a mixture of polymers in order to obtain mixtures exhibiting the desired properties of persistence in vivo, of rheology and of viscosity.

Another solution is recourse to interpenetrating polymer networks IPN or semi-interpenetrating polymer networks (semi-IPN) which make it possible to optimize the properties and to obtain compositions exhibiting the targeted properties, such as, for example, in application WO 2005/061611, filed by Innomed, which describes compositions formed of semi-interpenetrating networks of polysaccharides obtained by crosslinking at least one polysaccharide in the presence of at least one other polysaccharide which is not subject to crosslinking, or in U.S. Pat. No. 6,224,893, filed by MIT (Massachusetts Institute of Technology), which describes compositions formed of at least two polysaccharides which are subsequently crosslinked, for example by radiation, the polymers being crosslinked independently of one another but while being interpenetrating in order to form IPNs.

Injectable two-phase compositions have also been proposed. Patent application FR 2 733 427 describes compositions which comprise a continuous phase and a dispersed phase composed of insoluble fragments of a hydrogel. The aqueous continuous phase acts as vehicle for the injection of the fragments of the dispersed phase.

However, these various solutions are not completely satisfactory.

As regards the two-phase gels, the disadvantages in terms of side reactions have been described in the literature and their level of injectability is irregular as a result of the size of the particles, which can be difficult to control.

Furthermore, the main mechanisms involved in the decomposition of crosslinked polysaccharide gels are essentially surface and random mechanisms, which are all the more pronounced with regard to two-phase products exhibiting a greater decomposition surface area.

As regards products obtained by carrying out crosslinking on a mixture such as those described in application FR 2 865 737 or FR 2 861 734 or IPNs or semi-IPNs, although their perfect single-phase or the interpenetration of the networks guarantee good persistence in vivo and little or no side reaction, they do not make it possible to provide a satisfactory solution as there are technical difficulties in carrying out sometimes selective crosslinking reactions on mixtures, in particular of natural polymers, due, for example, to the variations in molecular weight. These products do not make it possible to guarantee perfect reproducibility of the physical properties from one batch to another, resulting in difficulty in operating industrially.

The present invention makes it possible to solve these various disadvantages.

The present invention consists of a biodegradable single-phase cohesive hydrogel, characterized in that it is composed of a homogeneous mixture of x identical or different polymers, crosslinked prior to their interpenetration by mixing, in the single-phase hydrogel form, said crosslinked polymers being insoluble in water and miscible with one another and x being between 2 and 5.

The cohesiveness and the single-phase nature of a gel according to the invention is understood to mean the property of said gel of retaining its stability and its unity without the possibility of separation of the constituent gels.

The term "mixing" is understood to mean a juxtaposition of x polymers without creation of a covalent bond between them. Interactions take place between the various polymers due to the presence of polar groups and of the aqueous medium; these interactions are of the low energy weak bond type involving forces such as, for example, intermolecular hydrogen bridges, indeed even ionic bonds.

The mixture thus obtained exhibits properties comparable to those of IPNs without being an IPN within the meaning of the IUPAC definition; this is because this definition excludes mixtures of networks crosslinked beforehand. In this instance, however, the cohesive and crosslinked beforehand gels are intimately mixed, generating weak interchain bonds between them.

They become indissociable from one another, thus generating a network of intertwined crosslinked gels, the cohesiveness of which is similar to that of IPNs.

Such a product exhibits the advantages of IPN networks without the disadvantages of employing the latter and makes it possible, by virtue of the use of a different degree of crosslinking for each constituent gel (or an identical degree of crosslinking, if the gels have very different molecular weights), to create more or less dense networks before their final hydration and, after mixing, to obtain a product having rheological properties which can be "adjusted" by measuring the properties of the various constituent gels before the mixing.

The crosslinking reactions can thus be carried out on isolated polymers, thus avoiding the problems of selectivity.

Implementation is thus easy and makes it possible to meet the final requirements while using natural products, the properties of which, in particular the molecular weight, can vary from one batch to another.

Furthermore, the implementation of the crosslinking conditions is simple, each gel being crosslinked independently of one another.

The mixture thus obtained will combine the advantages of each of the various constituent gels while minimizing their disadvantages, without bringing about the side effects observed with the use of compositions based on particles.

An optimization and a synergy in the resulting properties both in terms of injectability and in terms of persistence will be observed.

The synergy is obtained as a result of the optimization of the two parameters which act mutually on one another, low crosslinking being favorable to the injectability and unfavorable to the persistence and high crosslinking being favorable to the persistence and, a contrario, unfavorable to the injectability.

The respective properties of the networks complement one another; thus the gel with the highest elastic parameter will bring about an increase in the elastic parameter of the combination, in comparison with the least crosslinked gel. On the other hand, for the injectability (related to the viscosity of the product), the gel with the lowest level of injectability will make it possible to reduce the level of injectability of the combination. The characteristics of the final mixture are thus optimized, with a synergy of the elastic and viscous parameters of the mixtures obtained, which can be modified according to the respective proportions of each of the constituent gels and the pathology targeted.

It is thus possible to modify the viscosity of the mixture by adjusting the proportion of each of the x polymers. In the case of an excessively fluid final mixture, the addition of a highly crosslinked polymer will make it possible to obtain a suitable level of injectability. Conversely, in the case of an excessively viscous final mixture, the addition of a weakly crosslinked polymer will make it possible to reduce the degree of injectability of the combination.

Thus, whatever the application targeted, the use of finer needles than those generally used will make it possible to reduce inflammatory reactions and postinjection traumas.

As the characteristics are reproducible, the persistence of the gel will be known and predictable, apart from the factors of inter-individual variation, and the reproducibility of the injectability properties will make possible great control of the action and the elimination of a number of side effects.

A hydrogel, because of its makeup, will exhibit decomposition kinetics which depend on the number of gels mixed and on the degrees of crosslinking. This is because the decomposition kinetics depend on several parameters: the degree of crosslinking, the concentration of polymer and the molecular weights of the polymers used at the time of crosslinking.

The decomposition kinetics will be slowed down: this is because to homogeneously mix gels with variable degrees of persistence will make it possible to strengthen the overall persistence by an effect of "diluting" the random cleavages of the gel via either free radicals or enzymes (hyaluronidases, and the like) present in the dermis or the biological fluid replaced. The finished product thus manufactured will thus be more persistent for equivalent levels of injectability, while remaining perfectly biodegradable.

The persistence will also be optimized as a result of the interpenetration of the networks, increasing the density of crosslinks or chemical bonds while retaining the mechanical and chemical independence of the 2 to x crosslinked gels. Thus, random attack of the free radicals is statistically lower in comparison with a simple single-phase gel (just 1 network, faster weakening of the bonds at the surface, lower density of chemical bonds). Accessibility to the core of the gel will also be rendered much more difficult for decomposition by enzymes or via CD44 antigens. Furthermore, the use of different molecular weights in each single-phase gel crosslinked beforehand will make it possible to form networks with a more or less dense structure or meshwork and thus to further strengthen the persistence in vivo.

In one embodiment, the hydrogel according to the invention is characterized in that the polymers are selected from polysaccharides.

In one embodiment, the hydrogel according to the invention is characterized in that the polymers are selected from the group consisting of polylactic acids and their derivatives, N-vinylpyrrolidone, polyvinyl acids, polyacrylamides and acrylic polymers and biologically acceptable derivatives.

The polysaccharides are selected from the group consisting of hyaluronic acid, keratan, heparin, cellulose and cellulose derivatives, alginic acid, xanthan, carrageenan, chitosan, chondroitin and their biologically acceptable salts.

In one embodiment, at least one of the x polysaccharides is selected from the group consisting of hyaluronic acid and its biologically acceptable salts.

In another embodiment, the hydrogel according to the invention is characterized in that at least one of the x polysaccharides is selected from the group consisting of cellulose derivatives and their biologically acceptable salts.

In another embodiment, the hydrogel according to the invention is characterized in that at least one the x polysaccharides is selected from the group consisting of chondroitin and its biologically acceptable salts.

In another embodiment, the hydrogel according to the invention is characterized in that at least one of the x polysaccharides is selected from the group consisting of chitosan and its biologically acceptable salts and derivatives.

The polysaccharides which can be employed in the hydrogel according to the present invention are of any type known in the field and are preferably selected from those produced by bacterial fermentation. Generally, the polysaccharides which can be used in the context of the present invention exhibit a molecular weight MW of between approximately 0.02 and approximately 6 MDa, preferably of between approximately 0.04 and approximately 4 MDa and more preferably of between approximately 0.05 and approximately 3 MDa.

Preference is given in particular to hyaluronic acid and its salts, especially its salts acceptable from the physiological viewpoint, such as the sodium, potassium or calcium salts, advantageously the sodium salt.

Use is also advantageously made of chondroitin sulfate and its salts and cellulose derivatives, such as hydroxypropylmethylcellulose or carboxymethylcellulose, and the mixtures of two or more of them.

As sodium hyaluronate exhibits particularly advantageous properties due to its high operating recoil in intradermal injection, intra-articular injection, intra-peritoneal injection and other injections, and also has excellent rheological properties, the constituent gels of the hydrogel according to the invention are preferably based on sodium hyaluronate.

In one embodiment, the x polymers are identical.

In one embodiment, the x polymers are different.

In one embodiment, the hydrogel according to the invention is characterized in that x is equal to 2.

According to a specific embodiment, the first of the x polysaccharides is selected from the group consisting of hyaluronic acid and its salts, cellulose derivatives and their salts and xanthan and the second is selected from the group consisting of chondroitin sulfate and its salts, chitosan and its salts and derivatives, cellulose derivatives and their salts and alginic acids. In another specific embodiment, the first of the x polymers is selected from the group consisting of hyaluronic acid and its salts, cellulose derivatives and their salts and xanthan and the second is selected from the group consisting of polylactic acids and their derivatives and acrylic derivatives.

According to one embodiment, the first of the x polymers is selected from the group of sodium hyaluronate and the second is selected from the group consisting of chondroitin sulfate and its salts, chitosan and its salts and derivatives, cellulose derivatives and their salts and alginic acids.

In the hydrogel according to the present invention, the ratio by weight of the highly crosslinked polysaccharide to the weakly crosslinked polysaccharide can vary within very wide proportions, according to the nature of the polysaccharides used, their respective degrees of crosslinking and also the final properties targeted.

Generally, the proportion by weight of the highly crosslinked polysaccharide gel in the finished product is between approximately 0.1 and 99.9%, preferably from 5 to 50%, of gel 1 exhibiting a degree of crosslinking x1 and from 50 to 95% of gel 2 exhibiting a degree of crosslinking x2 or even more preferably from 10 to 40% of gel 1 exhibiting a degree of crosslinking x1 and from 60 to 90% of gel 2 exhibiting a degree of crosslinking x2.

The invention also relates to the process for the preparation of a biodegradable hydrogel according to the invention; this process comprises a stage of developing specifications which fix the rheological properties targeted as a function of the applications.

For the determination of the degree of persistence, an elasticity is targeted, that resulting from the degree of crosslinking, and, for the determination of the injectability, the viscosity at a high shear rate, also related to the degree of crosslinking, is set; these parameters depend on the starting materials, in particular on their molecular weight.

Having set the degrees of crosslinking and the respective proportions of the constituent gels, the process for the preparation of a biodegradable single-phase cohesive hydrogel according to the invention is characterized in that it comprises at least the stages of:

crosslinking a first polymer to a degree of crosslinking x1 crosslinking a second polymer to a degree of crosslinking x2 interpenetration by intimate mixing of the two polymers, hydration final interpenetration by final mixing after hydration.

The hydration is carried out, for example, by immersion in or addition of a buffered isotonic solution.

According to one embodiment, the process additionally comprises x stages of crosslinking x polymers before mixing the x crosslinked polymers.

The hydration is generally carried out in an aqueous medium by simple mixing of the mixture of crosslinked gels with an aqueous solution, advantageously a buffered physiological aqueous solution, so as to obtain a final concentration which can vary within very wide proportions according to the nature of the polysaccharides used, their respective degrees of crosslinking and also the use envisaged. The buffered solution which can be used can, for example, be an osmolar physiological solution exhibiting a pH of between approximately 6.8 and approximately 7.5.

This final concentration of total polysaccharides is generally between approximately 5 and approximately 100 mg/g, preferably between approximately 5 and approximately 50 mg/g, for example approximately 20 mg/g, of hydrogel.

The process of the present invention thus makes it possible to obtain a biodegradable single-phase cohesive hydrogel which can be injected and with a long lasting persistence.

In the preparation process as described above, the two crosslinking stages are carried out in a medium having a pH value which is identical or different. Each of these stages can be carried out in an acidic or basic medium, preferably in a basic medium, for example at a pH of between 8 and 14, preferably between 8 and 13.

The crosslinking reactions employed in the process of the invention are reactions well known to a person skilled in the art. For each polysaccharide and/or crosslinking agent, a person skilled in the art can develop and optimize the crosslinking conditions according to said polysaccharide and said crosslinking agent: degree of crosslinking, temperature, pH. However, it is specified that the crosslinking stages are carried out at constant pH, either acidic pH or basic pH, as indicated above.

The crosslinking agents which are involved in the crosslinking stages are generally bi- or polyfunctional crosslinking agents of various types and can, for example, be selected from DVS (divinyl sulfone) in an alkaline medium (see U.S. Pat. No. 4,582,865), bi- or polyfunctional epoxy compounds (see U.S. Pat. No. 4,716,154), carbodiimides, or formaldehyde (see GB 2 151 244).

Preference is given in particular to agents of bi- or polyepoxide type, the reactions taking place in a basic medium, to generate ether bonds with the —OH functional groups of the polysaccharide, or in an acidic medium, which gives rise to bonds of ester type. Patent application WO 2000/46253 successively uses these two pH conditions in order to optimize the crosslinking of the polysaccharide. However, it is preferable to carry out the crosslinking reactions under basic pH conditions since, in an aqueous medium, the ester bonds resulting from an acid medium are generally more labile than the ether bonds resulting from a basic medium.

Use may be made, as crosslinking agent, of an epoxide or its derivatives and in particular 1,4-butanediol diglycidyl ether (BDDE), diepoxyoctane or 1,2-bis(2,3-epoxypropyl)-

2,3-ethylene. Preference is very particularly given to the use of 1,4-butanediol diglycidyl ether (BDDE) for each of the crosslinking stages.

It should be understood that each of the crosslinking stages can be carried out with one or more crosslinking agents, it being possible for the latter to be identical or different in one or another of the stages, under the pH conditions indicated above.

After each of the crosslinking stages, the polysaccharides can advantageously be purified according to conventional purification techniques (for example by washing with a continuous stream of water, dialysis baths, and others), in order to remove the unreacted residual crosslinking agent.

In addition, the crosslinking stages can advantageously be followed by a neutralization stage (i.e., neutralization as far as a pH value of approximately 7), for example by addition of an appropriate amount of 1N hydrochloric acid.

In the hydrogel according to the invention, the x polymers exhibit different degrees of crosslinking, at least one of the x polymers exhibiting a degree of crosslinking x1 and at least one of the x polymers exhibiting a degree of crosslinking x2, and x1 being greater than x2.

In one embodiment, in the hydrogel according to the invention, the x polymers exhibit identical degrees of crosslinking, it being understood that the polymers can have different molecular weights.

In one embodiment, x1 and x2 are between 0.02 and 0.4 and preferably between 0.08 and 0.2.

On conclusion of the crosslinking, it may be advantageous to neutralize the gel obtained according to standard processes known in the field, for example by addition of acid, when the crosslinking is carried out in a basic medium, and by addition of a base, when the crosslinking is carried out in an acidic medium.

The mixture obtained on conclusion of the process can optionally be subjected to an additional hydration stage, in order to obtain a gel in the form of an injectable hydrogel suitable for the applications envisaged.

The invention relates to the use of a hydrogel according to the invention in the formulation of a viscosupplementation composition.

The invention relates to the use of a hydrogel according to the invention in the formulation of a composition for filling in wrinkles.

The applications targeted are more particularly the applications commonly observed in the context of injectable polysaccharide viscoelastic products used or which can potentially be used in the following pathologies or treatments:
- cosmetic injections: for filling in wrinkles, skin defects or defects of volume (cheekbones, chins, lips);
- treatment of osteoarthritis, injection into the
- joint to replace or supplement deficient synovial fluid;
- periurethral injection in the treatment of urinary incontinence by sphincter insufficiency;
- postsurgical injection for preventing peritoneal adhesions in particular;
- injection subsequent to surgery for far-sightedness by scleral incisions using a laser;
- injection into the vitreous cavity.

More particularly, in cosmetic surgery, according to its viscoelastic properties and properties of persistence, the hydrogel according to the invention can be used:
- for filling in fine, moderate or deep wrinkles and can be injected with thin needles (27-gauge, for example);
- as volumizing product with injection via needles with a larger diameter, for example from 22- to 26-gauge, and with a greater length (30 to 40 mm, for example); in this case, its cohesive nature will make it possible to guarantee that it is maintained at the site of the injection.

The hydrogel according to the invention also has an important application in joint surgery and in dental surgery for filling in periodontal pockets, for example.

These implementational examples are in no way limiting, the hydrogel according to the present invention being more widely provided for:
- filling in volumes;
- generating spaces within certain tissues, thus promoting their optimum functioning;
- replacing deficient physiological fluids.

The hydrogel according to the invention can also have an entirely advantageous application as matrix for releasing one (or more) active principle(s) dispersed beforehand within it. The term "active principle" is understood to mean any product which is active pharmacologically: medicinal active principle, antioxidant active principle (sorbitol, mannitol, and the like), antiseptic active principle, anti-inflammatory active principle, local anesthetic active principle (lidocaine, and the like), and the like.

In practice, the hydrogel according to the invention, preferably after purification and hydration to give the hydrogel, can be packaged, for example in syringes, and sterilized according to any means known per se (for example by autoclaving) in order to be sold and/or used directly.

According to another aspect, the present invention relates to a kit comprising a hydrogel according to the invention packaged in a sterile syringe.

The characteristics of the gels according to the invention are demonstrated in the examples below.

EXAMPLES

Degree of Crosslinking

The degrees of crosslinking x in the examples which follow are defined by:

x=number of moles of crosslinking agent introduced into the reaction medium/total number of disaccharide units introduced into the reaction medium.

Example 1

Crosslinking Gel 1

Stage a): Hydration of Sodium Hyaluronate Fibers in the form of a Noncrosslinked Gel Sodium hyaluronate fibers of injectable grade (1 g: molecular weight: approximately 2.7 MDa) are weighed out in a container. A 1% aqueous solution of sodium hydroxide in water (7.4 g) is added and the combined mixture is homogenized for approximately 1 hour using a spatula at ambient temperature and 900 mm Hg.

Stage b): Crosslinking

BDDE (65 mg) is added to the noncrosslinked sodium hyaluronate (NaHA) gel obtained in the preceding stage, the combined mixture being homogenized with a spatula for approximately 30 minutes at ambient temperature. The combined mixture is subsequently placed on a water bath at 50° C. for 2 h 20 in order to obtain a degree of crosslinking x1 of approximately 0.14.

Stage c): Neutralization, Purification

The crosslinked final gel is subsequently neutralized by addition of 1N HCl and placed in a phosphate buffer bath in order to stabilize the pH and to make possible its hydration or swelling as far as 30 mg/g of HA. An NaHa hydrogel crosslinked by the route conventionally used is thus obtained: G1 with an HA concentration of approximately 30 mg/g.

A portion of the gel is stored at this concentration and the other portion is diluted by addition of phosphate buffer in order to obtain, at the end, 20 mg/g of HA. This gel is subsequently homogenized before being filled into syringes which are sterilized by autoclaving: sterile syringes comprising gel G1 at 20 mg/g.

Crosslinking Gel 2

Stage a): Hydration of sodium hyaluronate fibers in the form of a noncrosslinked gel Sodium hyaluronate fibers of injectable grade (1 g; molecular weight: approximately 1.5 MDa) are weighed out and dried beforehand in a container. A 1% aqueous solution of sodium hydroxide in water (6.3 g) is added and the combined mixture is homogenized for approximately 1 hour using a spatula at ambient temperature and 900 mmHg.

Stage b): Crosslinking

BDDE (43 mg) is added to the noncrosslinked sodium hyaluronate (NaHA) gel obtained in the preceding stage, the combined mixture being homogenized with a spatula at ambient temperature and atmospheric pressure for approximately 30 minutes. The combined mixture is subsequently placed on a water bath at 50° C. for 2 h 20 in order to obtain a degree of crosslinking x2 of approximately 0.09.

Stage c): Neutralization, Purification

The crosslinked final gel is subsequently neutralized by addition of 1N HCl and placed in a phosphate buffer bath in order to stabilize the pH and to make possible its hydration or swelling as far as 30 mg/g of HA. An NaHa hydrogel crosslinked by the route conventionally used is thus obtained: G2 with an HA concentration of approximately 30 mg/g.

Example 2

Mixing/interpenetration of Gel 1 and Gel 2 in the proportions 10% G1-90% G2

Mixing/interpenetration of the gels G1 and G2 at 10%/90%

18 g of gel G2 at 30 mg/g are weighed out and 2 g of gel G1 obtained at the end of the preceding stage c) (G1 at 30 mg/g) are added thereto. 10 g of phosphate buffer are added and the 2 gels are placed under slow mechanical stirring for 1 h under hyperbaric pressure.

The mixture thus obtained is a homogeneous gel comprising 20 mg/g of HA and composed of 2 inter-penetrating networks; this gel is then packaged into syringes and autoclaved.

Example 3

Mixing/interpenetration of Gel 1 and Gel 2 in the proportions of 50% -50%

The gels obtained at the end of stage c) of each example above: gel 1 crosslinked to x1 approximately 0.14 and G2 crosslinked to x2 approximately 0.09, both with a concentration of approximately 30 mg/g of HA, are weighed out: 10 g of G1+10 g of G2.

10 g of phosphate buffer are also added and the 2 gels are placed under slow mechanical stirring for 1 h under hyperbaric pressure.

The mixture thus obtained is a homogeneous gel comprising 20 mg/g of HA and composed of 2 inter-penetrating networks; this gel is then packaged into syringes and autoclaved.

Example 4

Characterization of the gels of examples 1 and 2:
gel G1 crosslinked to x1,
mixture of 10% G1 and 90% G2 crosslinked to x2,
mixture of 50% G1 and 50% G2,
these 3 final products being all 3 at a final concentration of 20 mg/g of HA.

Characterization of the extrusion force or "injectability":

This test is carried out on the gels packaged into syringes and sterilized, with 27G1/2 needles, on a tensile compression testing machine with a rate of compression of 13 mm/min. The results of the extrusion forces of each of examples 1, 2 and 3 are given in the table below:

| Gel tested | Injectability (N) |
| --- | --- |
| Gel 1 | 37 |
| 10% Gel 1 + 90% Gel 2 | 21 |
| 50% Gel 1 + 50% Gel 2 | 31 |

A lower injectability of the interpenetrating networks of crosslinked gels in the comparison with the gel G1 alone is clearly observed.

Decomposition Test

These various gels were also characterized by an in vitro temperature decomposition test. This test makes it possible to simulate the subsequent in vivo persistence of the gels injected intradermally. It was developed on the basis of the specifications of the test of persistence described in patent FR 2 861 734. The gels were all placed in an oven at 93° C. for 14 h, 24 h and 48 h, with characterization of the elasticity after each time. The curves of the trend in the decomposition results for these various gels subsequently make it possible to evaluate the half-life of these various gels (period of time necessary to have G'=G'0/2, in hours, with G'0=elasticity at t0 of the gel characterized). The half-lives obtained are also given in the table below.

| Gel tested | ½ life (hours) |
| --- | --- |
| Gel 1 | 19 |
| 10% Gel 1 + 90% Gel 2 | 22.5 |
| 50% Gel 1 + 50% Gel 2 | 20.5 |

A greater decomposition is observed for Gel 1 alone, in comparison with the two interpenetrating networks of gels crosslinked beforehand.

Thus, for lower injectability and thus better control of the surgical action, the half-lives of the interpenetrating networks of gels obtained according to the invention are longer, guaranteeing a greater time of in vivo persistence.

Example 5

In order to confirm the cohesiveness and the single-phase nature of the hydrogels according to the invention, manual centrifuging tests of 3 times 5 minutes were carried out on the 10/90 and 50/50 mixtures comprising 20 mg/g of NaHA obtained in the preceding examples.

By comparison, a product of "two-phase" type, such as described in the prior art, was prepared according to the procedure of patent EP 0 466 300 with 50% of crosslinked NaHA particles dispersed in 50% of noncrosslinked NaHA viscous product, the two phases having been hydrated beforehand in phosphate buffer, comprising 20 mg/g of NaHA.

The products according to the invention obtained in the preceding examples do not show any separation on settling; the product, if ejected after the centrifuging operations, still has a homogeneous appearance.

On the other hand, the product of "two-phase" type shows, after centrifuging, separated particles at the bottom of the syringe. If the product is ejected from the syringe, the viscous product exits first, followed by the particles, which have no cohesiveness with one another, agglomerated at the bottom of the syringe, and which render the injectability particularly difficult.

Example 6

Mixing/interpenetrating of the gels G1 and G2 of example 1, in order to finally obtain gels and mixtures of gels at a concentration of 25.5 mg/g according to the process described in example 2 with adjustment of the NaHA concentrations by addition of phosphate buffer, in the following proportions:

IPN-Like Gel 1: 70% Gel 1 cross. x1+30% Gel 2 cross. x2
IPN-Like Gel 2: 50% Gel 1 cross. x1+50% Gel 2 cross. x2
IPN-Like Gel 3: 30% Gel 1 cross. x1+70% Gel 2 cross. x2

These gels are then packaged into syringes and sterilized by autoclaving.

Characteriziation of the extrusion force and of the elasticity of these IPN-like gels and of Gel 1 cross-linked to x1 and brought to an NaHA concentration of 25.5 mg/g:

The extrusion force is characterized on a Mecmesin tensile/compression testing machine under a rate of compression of 50 mm/min with 23G1 ¼ needles; the results are given in the table below.

The elasticity is characterized on a TA Instruments AR2000 Ex rheometer in oscillation at 25° C., the value of the elasticity being recorded at a frequency of 1 Hz; the results are given in the table below.

|  | Gel 1 at 25.5 mg/g | Inter-penetrating Gel 1 25.5 mg/g | Inter-penetrating Gel 2 25.5 mg/g | Inter-penetrating Gel 3 25.5 mg/g |
| --- | --- | --- | --- | --- |
| Extrusion force (N) 23G1¼ need. Rate 50 mm/min | 63 | 61 | 61 | 57 |
| Elasticity: G' (Pa) at 1 Hz | 200 | 225 | 244 | 265 |

It is observed, with regard to the 3 interpenetrating gels, that the extrusion forces are fairly close but all less than that of Gel 1, for increasing elasticities. Thus, the use of this technique of interpenetrating crosslinked gels makes it possible to obtain finished products of variable rheology: increasing elasticity (thus a better volumizing effect and a greater expected persistence) for lower levels of injectability.

Example 7

Synthesis of Gel 3: A Gel is Synthesized According to the Protocol/Operating Conditions of Example 1, Gel 1:

Stage a): Hydration of Sodium Hyaluronate Fibers in the form of a Noncrosslinked Gel This stage is identical to stage a) of the synthesis of Gel 1 of example 1.

Stage b): Crosslinking the Gel

This stage is identical to stage b) of the synthesis of Gel 1 of example 1, with 81 mg of PDDE. A Gel 3 with a degree of crosslinking x3 of approximately 0.17 is obtained.

Stage c): Neutralization, Purification

This stage is identical to stage c) of the synthesis of Gel 1 of example 1, in order to obtain a gel G3 with an HA concentration of approximately 30 mg/g.

A portion of the gel is stored at this concentration and the other portion is diluted by addition of phosphate buffer in order to finally obtain 24 mg/g of HA; this gel is subsequently homogenized before being filled into syringes which are sterilized by autoclaving: sterile syringes comprising gel G3 at 24 mg/g.

Interpenetration Gel 1/Gel 3 in the Proportions 80/20:

16 g of gel G1 at 30 mg/g are weighed out and 4 g of gel G3 at 30 mg/g, obtained at the end of the preceding stage c), are added thereto. 5 g of phosphate buffer are added and the 2 gels are placed under slow mechanical stirring for 1 h.

The mixture thus obtained is a homogeneous gel comprising 24 mg/g of HA and composed of 2 inter-penetrating networks; this gel is then packaged into syringes and autoclaved.

Characterization of the gels and interpenetrating gels described above:

Gel 3 with a degree of crosslinking x3, at 24 mg/g,

Gel 1 with a degree of crosslinking x1 and brought beforehand to 24 mg/g, packaged into syringes and sterilized, and the mixture of interpenetrating gels 80% Gel 1 +20% Gel 3, at 24 mg/g.

These gels are characterized by extrusion force. The tests are carried out with 27G1/2 needles on a Mecmesin tensile/compression testing machine with a rate of compression of 13 mm/min. The results for the extrusion forces of each of these gels are given in the table below.

These gels are also characterized by the in vitro temperature decomposition test described in example 4. The ½ lives obtained are also given in the table below.

|  | Extrusion force (N) 27G1/2 needle- 13 mm/min | ½ life (hours) |
| --- | --- | --- |
| Gel 1-x1-24 mg/g | 27 | 17 |
| Gel 3-x3-24 mg/g | 30 | 21 |
| 80% Gel 1/20% Gel 3-24 mg/g | 23 | 20.5 |

Thus, an equivalent persistence is observed for the interpenetrating gel and for Gel 3 crosslinked to the highest degree x3, for a lower level of injectability of this interpenetrating gel.

Example 8

Synthesis of 3 single-phase crosslinked gels according to examples 1 and 2:

Gel 4:

Stage a): identical to stage a) for the synthesis of Gel 1 of example 1 with 1 g of HA with a molecular weight of approximately 2.7 MDa and 6.8 g of a 1% aqueous solution of sodium hydroxide in water. The homogenization conditions are the same as in example 1.

Stage b): Crosslinking: identical to stage b) of the synthesis of Gel 1 of example 1 with 62 mg of BDDE. The combined product is brought to 50° C. on a water bath for 3 hours, in order to obtain a degree of crosslinking x4 of approximately 0.13.

Stage c): Neutralization, purification: identical to stage c) of the synthesis of Gel 1 of example 1, in order to obtain a Gel 4 at 30 mg/g. A portion of the gel is stored at this concentration and the other portion is diluted by addition of phosphate buffer in order to finally obtain 24 mg/g of HA; this gel is subsequently homogenized before being filled into syringes which are sterilized by autoclaving: sterile syringes comprising gel G4 at 24 mg/g.

Gel 5:

Stage a): identical to stage a) of the synthesis of Gel 4.

Stage b): Crosslinking: identical to stage b) of the synthesis of Gel 4 with 80 mg of BDDE. The combined product is brought to 50° C. on a water bath for 3 hours, in order to obtain a degree of crosslinking x5 of approximately 0.17.

Stage c): Neutralization, purification: identical to stage c) of the synthesis of Gel 4 in order to obtain a Gel 5 at 30 mg/g. A portion of the gel is stored at this concentration and the other portion is diluted by addition of phosphate buffer in order to finally obtain 24 mg/g of HA; this gel is subsequently homogenized before being filled into syringes which are sterilized by autoclaving: sterile syringes comprising gel G5 at 24 mg/g.

Gel 6:

Stage a): identical to stage a) of the synthesis of Gel 2 of example 1 with 1 g of sodium hyaluronate with a molecular weight of approximately 1.3 MDa and 5.7 g of a 1% aqueous solution of sodium hydroxide in water.

Stage b): Crosslinking

Identical to stage c) of example 1 with 41 mg of BDDE. The combined product is brought to 50° C. on a water bath for 3 hours, in order to obtain a degree of crosslinking x6 of approximately 0.09.

Stage c): Neutralization, Purification

Identical to stage c) of the synthesis of the preceding Gel 5 in order to obtain a Gel 6 at 30 mg/g. A portion of the gel is stored at this concentration and the other portion is diluted by addition of phosphate buffer in order to finally obtain 24 mg/g of HA; this gel is subsequently homogenized before being filled into syringes which are sterilized by autoclaving: sterile syringes comprising gel G6 at 24 mg/g.

Interpenetration of Gels 4, 5 and 6 (Respective Proportions: 25%, 5% and 70%)

5 g of gel G4 at 30 mg/g are weighed out, 1 g of gel G5 at 30 mg/g is weighed out and then 14 g of gel G6 at 30 mg/g are weighed out. 5 g of phosphate buffer are added and the 3 gels are placed under slow mechanical stirring for 1 h. A final single-phase gel G7 comprising 24 mg/g of sodium hyaluronate and composed of 3 interpenetrating single-phase crosslinked gels is thus obtained.

Characterization of the elasticity and of the extrusion force of the 3 conventional gels and of the interpenetrating mixture:

according to the methods described in the preceding examples.

|  | Gel 4 24 mg/g | Gel 5 24/mg | Gel 6 24 mg/g | Gel G7 (intelpenetrating 4, 5 and 6) 24 mg/g |
|---|---|---|---|---|
| Extrusion force (N) 23G1¼ need. Rate 13 mm/min | 31 | 38 | 18 | 16 |
| Elasticity: G' (Pa) at 1 Hz | 245 | 415 | 186 | 224 |

Gel G7, composed of the interpenetration of the 3 crosslinked gels (G4, G5 and G6), has the lowest extrusion force, for an elasticity value greater by approximately 20% than that of the gel G6 with a close but slightly greater level of injectability.

Its elasticity is lower by only 10% with respect to that of Gel 4, the level of injectability of which is greater by more than 40%.

The advantage of these interpenetrating gels is clearly perceived.

Example 9

Interpenetration of Crosslinked HA and Crosslinked CMC (Carboxymethyl Cellulose) Gels Crosslinked CMC gel: gel G8

Stage a): Hydration of NaCMC in the Form of a Noncross-Linked Gel 1 g of sodium carboxymethyl cellulose with an intrinsic viscosity (supplied by Sigma) is weighed out in a container. A 1% aqueous solution of sodium hydroxide in water (7.3 g) is added and the combined mixture is homogenized for approximately 90 minutes using a spatula at ambient temperature and 900 mmHg.

Stage b): Crosslinking

BDDE (37 mg) is added to the noncrosslinked CMC gel obtained in the preceding stage, the combined mixture being homogenized with a spatula for approximately 30 minutes at ambient temperature. The combined mixture is subsequently placed on a water bath at 50° C. for 3 h in order to obtain a degree of crosslinking x8 of approximately 0.19.

Stage c): Neutralization, Purification

The crosslinked final gel is subsequently neutralized by addition of 1N HCl and placed in a phosphate buffer bath in order to stabilize the pH and to make possible its hydration or swelling as far as 45 mg/g of CMC. An NaCMC hydrogel crosslinked by the route conventionally used is thus obtained: G8 with a CMC concentration of approximately 45 mg/g.

Interpenetration of HA gel G1 and CMC gel G8

The HA gel G1 crosslinked to a level of 0.14, at a concentration of 30 mg/g, is added in various proportions to the crosslinked NaCMC gel G8, the phosphate buffer is added in order to adjust the final concentrations to 26 mg/9 of HA and 37 mg/g of CMC and the 2 gels are placed under slow mechanical stirring with the phosphate buffer for 1 hour under hyperbaric pressure. 3 interpenetrating gels as described below are thus obtained:

Gel 9: 30% G1+70% G8
Gel 10: 50% G1+50% G8
Gel 11: 70% G1+30% G8

These 3 interpenetrating gels are subsequently packaged into syringes and characterized by rheology (elastic modulus G') and by injectability under a rate of 13 mm/min with 27G1/2 needles. The gels G1 and G8 are also adjusted to the concentrations of 26 mg/g for G1 and 37 mg/g for G8 in order to compare them with the 3 interpenetrating gels.

The results of the characterizations are combined in the table below.

|  | G1 (cross-linked HA, 26 mg/g) | G8 (cross-linked CMC, 37 mg/g) | G9 Inter-penetrating gel 30% G1 + 70% G8 | G10 Inter-penetrating gel 50% G1 + 50% G8 | G11 Inter-penetrating gel 70% G1 + 30% G8 |
|---|---|---|---|---|---|
| Elastic modulus G' at 1 Hz (Pa) | 235 | 265 | 240 | 243 | 264 |
| Injectability 27G1/2 need. (N) | 33 | 18 | 18 | 12 | 16 |

A virtually constant elastic modulus is observed for the 5 interpenetrating or non-interpenetrating gels but with lower levels of injectability for the inter-penetrating gels than for each independent crosslinked gel, with a high synergistic effect with regard to the 50/50 mixture (Gel 10).

The invention claimed is:

1. A process of preparing a biodegradable single-phase cohesive hydrogel composition, comprising:
   preparing 2 to 5 hydrogels that are independently cross-linked so that each hydrogel has a degree of crosslinking in a range from 0.02 to 0.4; and
   mixing the 2 to 5 hydrogels to obtain a homogenous mixture of 2 to 5 intertwined hydrogels that interpenetrate each other to form a single phase without covalent bonding between the hydrogels, wherein:
   each hydrogel is prepared by a process that comprises independently crosslinking a polymer; and
   the total polymer concentration of the composition is in a range from 5 to 50 mg/g.

2. The process according to claim 1, wherein crosslinking is performed using a bi- or polyfunctional crosslinking agent selected from the group consisting of bi- or polyfunctional epoxy compounds and divinyl sulfone.

3. The process according to claim 1, wherein a crosslinking agent used in each independent crosslinking is identical.

4. The process according to claim 1, wherein the homogenous mixture is of 2 intertwined hydrogels.

5. The process according to claim 1, wherein each hydrogel has a different degree of crosslinking within the range from 0.02 to 0.4.

6. The process according to claim 1, wherein each hydrogel has an identical degree of crosslinking within the range from 0.02 to 0.4.

7. The process according to claim 1, wherein each hydrogel has a degree of crosslinking in a range from 0.08 to 0.2.

8. The process according to claim 1, wherein each polymer has a different molecular weight prior to crosslinkage.

9. The process according to claim 1, wherein each polymer is different in type.

10. The process according to claim 1, wherein each polymer is a polysaccharide.

11. The process according to claim 10, wherein each polysaccharide is selected from the group consisting of hyaluronic acid, keratan, heparin, cellulose, cellulose derivatives, alginic acid, xanthan, carrageenan, chitosan, chondroitin, and biologically acceptable salts thereof.

12. The process according to claim 10, wherein each polysaccharide is hyaluronic acid or a biologically acceptable salt thereof.

13. The process according to claim 10, wherein at least one polysaccharide is selected from the group consisting of cellulose derivatives and biologically acceptable salts thereof.

14. The process according to claim 10, wherein at least one polysaccharide is selected from the group consisting of chondroitin and biologically acceptable salts thereof.

15. The process according to claim 10, wherein at least one polysaccharide is selected from the group consisting of chitosan and biologically acceptable salts thereof.

16. The process according to claim 1, further comprising adding one or more active principles so as to incorporate the active principles into the homogenous mixture of 2 to 5 intertwined hydrogels, wherein the active principles are selected from the group consisting of antioxidants, antiseptics, anti-inflammatories, local anesthetics, and mixtures thereof.

17. The process according to claim 1, further comprising adding at least one antioxidant so as to incorporate the antioxidant into the homogenous mixture of 2 to 5 intertwined hydrogels, wherein the antioxidant is selected from the group consisting of mannitol and sorbitol.

18. The process according to claim 1, further comprising adding a local anesthetic so as to incorporate the local anesthetic into the homogenous mixture of 2 to 5 intertwined hydrogels.

19. The process according to claim 1, wherein the composition is formulated as a viscosupplementation composition.

20. The process according to claim 1, wherein the composition is formulated for filling in wrinkles.

21. The process according to claim 1, wherein the homogenous mixture is of 2 intertwined hydrogels and each polymer of the hydrogels is hyaluronic acid or a biologically acceptable salt thereof.

22. The process according to claim 21, further comprising adding at least one antioxidant so as to incorporate the antioxidant into the homogenous mixture of 2 intertwined hydrogels, wherein the antioxidant is selected from the group consisting of mannitol and sorbitol.

* * * * *

UNITED STATES PATENT AND TRADEMARK OFFICE
CERTIFICATE OF CORRECTION

| | |
|---|---|
| PATENT NO. | : 10,207,024 B2 |
| APPLICATION NO. | : 15/812588 |
| DATED | : February 19, 2019 |
| INVENTOR(S) | : Estelle Marie Piron et al. |

Page 1 of 1

It is certified that error appears in the above-identified patent and that said Letters Patent is hereby corrected as shown below:

On the Title Page

ITEM (60), Lines 4-5:
Delete "Dec. 8, 2007," and insert --Dec. 8, 2008,--

Signed and Sealed this
Thirteenth Day of August, 2019

Andrei Iancu
*Director of the United States Patent and Trademark Office*